US007611883B2

(12) United States Patent
Cranenburgh (10) Patent No.: US 7,611,883 B2
(45) Date of Patent: Nov. 3, 2009

(54) PLASMID MAINTENANCE

(75) Inventor: Rocky Marc Cranenburgh, Staffordshire (GB)

(73) Assignee: Cobra Biologics Limited (GB)

( * ) Notice: Subject to any disclaimer, the term of this patent is extended or adjusted under 35 U.S.C. 154(b) by 0 days.

(21) Appl. No.: 10/579,981

(22) PCT Filed: Nov. 22, 2004

(86) PCT No.: PCT/GB2004/004929

§ 371 (c)(1),
(2), (4) Date: Jan. 7, 2007

(87) PCT Pub. No.: WO2005/052167

PCT Pub. Date: Jun. 9, 2005

(65) Prior Publication Data

US 2007/0110721 A1    May 17, 2007

(30) Foreign Application Priority Data

Nov. 20, 2003   (GB)   ................................ 0327056.8

(51) Int. Cl.
*C12N 15/64* (2006.01)
(52) U.S. Cl. ................... 435/252.3; 435/480; 435/481; 435/486; 435/488; 435/91.4
(58) Field of Classification Search ..................... None
See application file for complete search history.

(56) References Cited

U.S. PATENT DOCUMENTS

| 6,413,768 | B1 | 7/2002 | Galen | ....................... 435/320.1 |
| 2006/0063232 | A1 | 3/2006 | Grabherr et al. | ........... 435/69.1 |

FOREIGN PATENT DOCUMENTS

| EP | 0 851 932 B1 | 7/1998 |
| WO | 97/14805 A2 | 4/1997 |
| WO | 02/079467 A2 | 10/2002 |

OTHER PUBLICATIONS

Shohat, et al. (1987) Inhibition of Cell Growth Mediated by Plasmids Encoding p53. Oncogene, v.1(3):277-283.*
Hu and Davidson (1987) The Inducible Lac Operator-Repressor System is Functional in Mammalian Cells. Cell, v.48(4):555-66.*
Adhya, S., "The Galactose Operon," in *Escherichia coli* and *Salmonella typhimurium*, Eds. J. L. Ingraham et al., 1987, Amer. Soc. Micro., 1503-1512.
Altboum, Z. et al., "Attenuated *Shigella flexneri* 2a Delta guaBA strain CVD 1204 expressing enterotoxigenic *Escherichia coli* (ETEC) CS2 and CS3 fimbriae as a live mucosal vaccine against Shigella and ETEC infection," *Infect Immun.*, 2001, 69(5), 3150-3158.
Baik, H. S. et al., "The acid tolerance response of *Salmonella typhimurium* provides protection against organic acids," *Microbiology*, 1996, 142(Pt 11), 3195-3200.

Bebbington, C. R. et al., "High-level expression of a recombinant antibody from myeloma cells using a glutamine synthetase gene as an amplifiable selectable marker," *Bio/Technology*, 1992, 10(2), 169-175.
Beckwith, J., "The Lactose Operon," in *Escherichia coli* and *Salmonella typhimurium*, Eds. Ingraham, J. L. et al., 1987, Amer. Soc. Micro., 1444-1452.
Bijlsma, J. J. et al., "Identification of loci essential for the growth of *Helicobacter pylori* under acidic conditions," *J. Infect. Dis.*, 2000, 182(5), 1566-1599, Epub Oct. 9, 2000.
Borezee, E. et al., "SvpA, a novel surface virulence-associated protein required for intracellular survival of *Listeria monocytogenes*," *Microbiology*, 2001, 147(Pt 11), 2913-2923.
Bouvier, J. et al., "Nucleotide sequence and expression of the *Escherichia coli* dapB gene," *J. Biol. Chem.*, 1984, 259(23), 14829-14834.
Brantl, S., "Antisense RNAs in plasmids: Control of replication and maintenance," *Plasmid*, Nov. 2002, 48(3), 165-173.
Burke, M. et al., "Mutant *Escherichia coli* arginine repressor proteins that fail to bind L-arginine, yet retain the ability to bind their normal DNA-binding sites," *Mol. Microbiol.*, 1994, 13(4), 609-618.
Castanie-Cornet and Foster, J. W., "*Escherichia coli* acid resistance: cAMP receptor protein and a 20 bp cis-acting sequence control pH and stationary phase expression of the gadA and gadBC glutamate decarboxylase genes," *Microbiology*, 2001, 147(Pt 3), 709-715.
Cesareni, G. et al., "Control of Co1E1 DNA replication: the rop gene product negatively affects transcription from the replication primer promoter," *Proc. Natl. Acad. Sci. USA*, Oct. 1982, 79, 6313-6317.
Chan, P. T. et al., "Nucleotide sequence and gene organization of Co1E1 DNA," *J. Biol. Chem*, 1985, 260(15), 8925-8935.
Cohen, J. S., "Designing antisense oligonucleotides as pharmaceutical agents," *Trends in Pharm. Sci.*, 1989, 10(11), 435-437.
Cooney, M. et al., "Site-specific oligonucleotide binding represses transcription of the human c-myc gene in vitro," *Science*, 1988, 241(4864), 456-459.
Cotter, P. D. et al., "Analysis of the role of the *Listeria monocytogenes* F0F1 -AtPasc operon in the acid tolerance response," *Int. J. Food Microbiol.*, 2000, 60(2-3), 137-146.
Cranenburgh, R. M. et al., "*Escherichia coli* strains that allow antibiotic-free plasmid selection and maintenance by repressor titration," *Nucl. Acids Res.*, 2001, 29(5), e26-e27.
Cronan et al., "Biosynthesis of membrane lipids," in *Escherichia coli* and *Salmonella typhimurium*: cellular and molecular biology, vol. 1, Neidhardt, F. C. (ed.) American Society of Microbiology, Washington, D. C., 1987, pp. 474-497.
del Solar, G. et al., "Replication and control of circular bacterial plasmids," *Microbiol. And Molec. Biol. Rev.*, 1998, 62(2), 434-363.

(Continued)

*Primary Examiner*—Sean R McGarry
*Assistant Examiner*—Jennifer Pitrak
(74) *Attorney, Agent, or Firm*—Woodcock Washburn LLP (57) ABSTRACT

The invention relates to a system for stable maintenance of a plasmid, to host cells for use in this system and to methods of using the system to obtain a plasmid useful in medical applications. In particular, the invention provides transformed host cell containing: i) a chromosomal gene which inhibits cell growth; and ii) a plasmid encoding an antisense sequence, wherein the antisense sequence encoded by the plasmid inhibits the action of the chromosomal gene, thereby permitting cell growth and a method for stable maintenance of a plasmid in a host cell in vivo.

37 Claims, 3 Drawing Sheets

OTHER PUBLICATIONS

Delihas, N., "Regulation of Gene Expression by Trans-encoded Antisense RNAs," *Molecular Microbiology*, 1995, 15(3), 411-414.

Dervan, P. B. et al. "Second structural motif for recognition of DNA by oligonucleotide-directed triple-helix formation," *Science*, 1991, 251(4999), 1360-1363.

Dickson, R. C. et al., "Genetic regulation: the Lac control region," *Science*, 1975, 187(4171), 27-35.

Dunn, T. M. et al., "An operator at -280 base pairs that is required for repression of araBAD operon promoter: addition of DNA helical turns between the operator and promoter cyclically hinders repression," *Proc. Natl. Acad. Sci.*, 1984, 81 (16), 5017-5020.

Feberwee, A. et al., "The spread of *Salmonella gallinarum* 9R vaccine strain under field conditions," *Avian Dis.*, 2001, 45(4), 1024-1029.

Galen, J. E. et al., "Optimization of plasmid maintenance in the attenuated live vector vaccine strain *Salmonella typhi* CVD 908-htrA," *Infect. Immun.*, 1999, 67(12), 6424-6433.

Garmory, H. S. et al., "*Salmonella* vaccines for use in humans: present and future perspectives," *FEMS Microbiology Reviews*, 2002, 26(4), 339-353.

Gossen, M. et al., "Inducible gene expression systems for higher eukaryotic cells," *Current Opinions in Biotechnology*, 1994, 5(5), 516-520.

Hanna, M. N. et al., "uvrA is an acid-inducible gene involved in the adaptive response to low pH in *Streptococcus mutans*," *J. Bacteriol.*, 2001, 183(20), 5964-5973.

Hare, D. L. et al., "Regulated high-level expression of the *Herpes simplex* type I thymidine kinase gene in *Escherichia coli*," *Gene*, 1984, 32, 117-128.

Hiszczynska-Sawicka et al., "Effect of Integration Host Factor on RNA II Synthesis in Replication of Plasmid Containing *orip* 15A," *Plasmid*, 1998, 40, 150-157.

Hochschild, A. et al., "How lambda repressor and lambda Cro distinguish between OR1 and OR3," *Cell*, 1986, 47(5), 807-816.

Introduction to Lambda Phages, in Current Protocols in Molecular Biology, Eds. Ausubel, et al., 1994, Section III, Unit 1.9.

Lee, J. S. et al., "Complexes formed by (pyrimidine)n . (purine)n DNAs on lowering the pH are three-stranded," *Nucleic Acids Res.*, 1979, 6(9), 3073-3091.

Liang, S. et al., "Activities of constitutive promoters in *Escherichia coli*," *J. Mol. Biol.*, 1999, 292, 19-37.

Link, A. J. et al., "Methods for generating precise deletions and insertions in the genome of wild-type *Escherichia coli*: application to open reading frame characterization," *J. Bacteriol.*, 1997, 179(20), 6228-6237.

McMacken et al. In *Escherichia coli* and *Salmonella typhimurium*: cellular and molecular biology, Neidhardt, F. C. (ed.) American Society of Microbiology, Washington, D. C. 1987, pp. 564-612.

Morona, R. et al., "Construction of plasmid vectors with a non-antibiotic selection system based on the *Escherichia coli* thyA+ gene: application to cholera vaccine development," *Gene*, 1991, 107, 139-144.

Murphy, K. C., "Use of bacteriophage lambda recombination functions to promote gene replacement in *Escherichia coli*," *J. Bacteriol.*, 1998, 180(8), 2063-2071.

Ogden, K. L. et al., "An Adjustable Expression System for Controlling Growth Rate, Plasmid Maintenance, and Culture Dynamics," *Biotech. Bioeng.*, 1992, 40, 1027-1038.

Okano, H. et al., "Myelin basic protein gene and the function of antisense RNA in its repression in myelin-deficient mutant mouse," *J. Neurochem*, 1991, 56(2), 560-567.

Oyston, P. C. et al., "Immunization with live recombinant *Salmonella typhimurium* aroA producing F1 antigen protects against plague," *Infection and Immunity*, 1995, 63(2), 563-568.

Richaud, C. et al., "Regulation of expression and nucleotide sequence of the *Escherichia coli* dapD gene," *J. Biol. Chem.*, 1984, 259(23), 14824-14828.

Richaud, F. et al., "Chromosomal location and nucleotide sequence of the *Escherichia coli* dapA gene," *J. Bacteriol.*, 1986, 166, 297-300.

Rippere-Lampe, K. E. et al., "Mutation of the gene encoding cytotoxic necrotizing factor type 1 (cnf(1)) attenuates the virulence of uropathogenic *Escherichia coli*," *Infect. Immun.*, 69(6), 3954-3964.

Ryan, E. T. et al., "Development of a DeltaglnA balanced lethal plasmid system for expression of heterologous antigens by attenuated vaccine vector strains of *Vibrio cholerae*," *Infect. Immun.*, 2000, 68, 221-226.

Schlief, R., "The L-Arabinose Operon," in *Escherichia coli* and *Salmonella typhimurium*, Eds. J. L. Ingraham et al., 1987, Amer. Soc. Micro., 1473-1481.

Scott, J. R. et al., "Regulation of plasmid replication," *Microbiol. Rev.*, 1984, 48, 1-23.

Sheehan, B. et al., "A single substitution in the putative helix-turn-helix motif of the pleiotropic activator PrfA attenuates *Listeria monocytogenes* virulence," *Mol. Microbiol.*, 1996, 20(4), 785-797.

Skogman, S. G. et al., "Temperature-dependent retention of a tryptophan-operon-bearing plasmid in *Escherichia coli*," *Gene*, 1984, 31(1-3), 117-122.

Tacket, C. O. et al., "Safety and immunogenicity in humans of an attenuated *Salmonella typhi* vaccine vector strain expressing plasmid-encoded hepatitis B antigens stabilized by the Asd-balanced lethal vector system," *Infect. Immun.*, 1997, 65(8), 3381-3385.

Titball, R. W. et al., "Expression of the *Yersinia pestis* capsular antigen (F1 antigen) on the surface of an aroA mutant of *Salmonella typhimurium* induces high levels of protection against plague," *Infection and Immunity*, 1997, 65(5), 1926-1930.

Tomizawa, J. et al., "Control of ColE1 Plasmid Replications: Enhancement of Binding of RNA I to the Primer Transcript by the Rom Protein," *Cell*, 1984, 38, 871-878.

Toso, J. F. et al., "Phase I study of the intravenous administration of attenuated *Salmonella typhimurium* to patients with metastatic melanoma," *J. Clin. Oncol.*, 2002, 20, 142-152.

Vemulapalli, R. et al., "*Brucella abortus* strain RB51 as a vector for heterologous protein expression and induction of specific Th1 type immune responses," *Infect. Immun.*, 2000, 68(6), 3290-3296.

Walsh, C. T., "Enzymes in the D-alanine branch of bacterial cell wall peptidoglycan assembly," *J. Biol. Chem.*, 1989, 264(5), 2393-2396.

Wang, M-D. et al., "Cloning of genes that suppress an *Escherichia coli* K-12 alanine auxotroph when present in multicopy plasmids," *J. Bacteriol.*, 1987, 169(12), 5610-5614.

Weaver, K. E. et al., "Functional analysis of the *Enterococcus faecalis* plasmid pAD1-encoded stability determinant par," *Molecular Microbiology*, 1996, 20(1), 53-63.

Williams, S. G. et al., "Repressor titration: a novel system for selection and stable maintenance of recombinant plasmids," *Nucl. Acids Res.*, 1998, 26(9), 2120-2124.

Yanofsky, C. et al, "The tryptophan Operon," in *Escherichia coli* and *Salmonella typhimurium*, Eds. J. L. Ingraham et al., 1987, Amer. Soc. Micro., 1453-1472.

Zengel, J. M. et al., "High-efficiency, temperature-sensitive suppression of amber mutations in *Escherichia coli*," *J. Bacteriol.*, 1981, 145, 459-465.

Zielenkiewicz, U. et al., "Mechanisms of plasmid stable maintenance with special focus on plasmid addiction systems," *Acta Biochimica Polonica*, 2001, 48(4), 1003-1023.

\* cited by examiner

Figure 1:

pUC18 ori
597 bp

Figure 2:

Repressor oriSELECT

Figure 3:

Toxin oriSELECT

Figure 4:

Double antisense oriSELECT

PLASMID MAINTENANCE

FIELD OF THE INVENTION

The invention relates to a system for stable maintenance of a plasmid, to host cells for use in this system and to methods of using the system to obtain a plasmid useful in medical applications.

All documents referred to herein are incorporated by reference.

BACKGROUND OF THE INVENTION

Plasmids are routinely used in the preparation of recombinant proteins and in the preparation of DNA for gene therapy purposes. The stable maintenance of a plasmid in a host cell is important for the efficient preparation of these products. However, extrachromosomal DNA carried in host cells is inherently unstable due to an increased metabolic burden on cells containing the plasmid compared to cells that are plasmid-free. To maintain plasmid stability and decrease metabolic burden, plasmids have been engineered to contain dominant selectable markers.

The conventional method of maintaining plasmids in cells in culture is to include an antibiotic resistance gene on the plasmid and to culture the cells in the presence of the appropriate antibiotic. For cells or plasmids intended for therapeutic use, this has the disadvantage that use of plasmid containing the antibiotic resistance gene may contribute to the spread of antibiotic resistance.

Some methods of plasmid maintenance have attempted to exploit naturally-occurring post segregational killing mechanisms controlled by plasmid-borne genes. For example, the hok/sok, srnB and pnd systems involve a killer protein encoded by a stable mRNA and regulated by a small, unstable antisense RNA that binds to the killer RNA and inactivates it. The killer RNA is retained in plasmid-free segregants after the antisense RNA has degraded and is translated into the lethal protein. Plasmid maintenance using the hok/sok system was investigated in the attenuated live vector vaccine strain *Salmonella typhi* CDV 908 htr-A (Galen et al, 1999, Infect. Immunol, 67: 6424-6433). However, such post-segregational killing mechanisms do not enable plasmid selection following transformation and are therefore still dependent on the presence of an antibiotic resistance gene on the plasmid.

Some alternative methods for maintaining and selecting plasmids without antibiotic selection have been developed in which the plasmid encodes a gene complementing a host cell auxotrophy. For example, a host cell may be a mutant cell which is unable to synthesise an essential amino acid metabolite and which can only survive in medium lacking the amino acid in the presence of a plasmid comprising a gene encoding the missing element for synthesis of this amino acid (Wang M-D et al, 1987, J. Bacteriol., 169: 5610-5614). However, this approach limits the composition of the growth medium since the amino acid must be omitted. An alternative method, which can be used in complex media, uses a mutant host cell with a thermosensitive tRNA synthetase gene which can only survive at non-permissive temperatures if a plasmid comprising the wild-type tRNA synthetase gene is present (Skogman et al, 1984, Gene 31: 117-122). Another selection method uses a plasmid-borne tRNA gene to complement nonsense mutations in essential chromosomal genes in a mutant host cell (Zengel et al, 1981, J. Bacteriol, 145: 459-465). Alternatively, a gene that increases the metabolic burden on a cell, such as the pil operon, may be placed on the host chromosome such that the host cell only survives in the presence of a plasmid encoding the corresponding repressor protein (Ogden et al, 1992, Biotech. Bioeng., 40:1027-1038).

EP 0851932 describes a method of maintaining plasmids within host cells in in vitro culture by means of operator repressor titration. The method involves engineering a host cell, such that it contains a first chromosomal gene encoding a repressor and a second chromosomal gene essential for cell growth that has an operator sequence for the repressor in its control region. In the absence of a plasmid, expression of the second chromosomal gene is inhibited by binding of the repressor to the operator and the cell dies. The plasmids for maintenance in this host cell are engineered to contain the operator sequence such that in the presence of the plasmid, the repressor is titrated away from the operator for the gene essential for cell growth, the gene is expressed and the cell survives. This mechanism is also described in Williams et al (Nucleic Acids Research, 1999, 26(9): 2120-2124) and in Cranenburgh et al (Nucleic Acid Research, 2001, 29(5): e26-e27).

Although some mechanisms of plasmid maintenance and selection which do not rely on antibiotic selection are known, there remains a need for the development of additional methods in view of the increasing importance of plasmids in the production of DNA and recombinant proteins for therapeutic applications. In addition, the systems of plasmid maintenance and selection developed to date require the use of plasmids which have been specially modified for use in these systems. There remains a need for a system of plasmid maintenance and selection which does not involve antibiotic resistance and which employs plasmids that are common in the art and do not require special modification.

SUMMARY OF THE INVENTION

According to a first aspect of the invention, there is provided a transformed host cell containing
  i) a chromosomal gene which inhibits cell growth; and
  ii) a plasmid encoding an antisense sequence, wherein said antisense sequence encoded by the plasmid inhibits the action of the chromosomal gene, thereby permitting cell growth.

Preferably, the antisense sequence encoded by the plasmid is encoded by the origin of replication of the plasmid although it may be encoded by other areas of the plasmid.

As used herein, the term "antisense sequence" refers to a nucleic acid sequence that is substantially complementary to its target sequence and has the ability to specifically hybridize to that target sequence. Preferably, the antisense sequence encoded by the plasmid hybridises to its target sequence under stringent conditions. High stringency hybridisation conditions are defined as overnight incubation at 42° C. in a solution comprising 50% formamide, 5×SSC (150 mM NaCl, 15 mM trisodium citrate), 50 mM sodium phosphate (pH7.6), 5× Denhardts solution, 10% dextran sulphate, and 20 microgram/ml denatured, sheared salmon sperm DNA, followed by washing the filters in 0.1×SSC at approximately 65° C.

As used herein, "cell growth" refers to increasing numbers of cells in a culture medium over time and to cell survival, where the number of live cells does not decrease over time. By "inhibits cell growth" is meant that the chromosomal gene is either lethal to the cell, such that the number live cells in a culture medium decreases over time, or that it prevents cell growth, such that the numbers of cells in a culture medium does not increase over time.

Growth of the transformed host cell according to this first aspect of the invention is dependent on the presence of the plasmid, resulting in selection of cells maintaining the plasmid. If the plasmid is lost from the host cell, the action of the chromosomal gene will no longer be prevented by the antisense sequence encoded by the plasmid and cell growth will be inhibited. In some embodiments, only a single copy of the plasmid may be required for expression of the chromosomal gene to be inhibited, thereby permitting cell growth. In other embodiments, it may be necessary for the plasmid to be present in multiple copies in order for expression of the chromosomal gene to be inhibited.

The chromosomal gene may inhibit cell growth directly. For example, transcription and translation of the chromosomal gene may produce a protein that is lethal to the cell, such as a toxin. Alternatively, the chromosomal gene may inhibit cell growth indirectly. For example, transcription and translation of a chromosomal gene may produce a repressor protein that inhibits transcription and translation of a protein that is essential for cell growth encoded by a second chromosomal gene. Transcription of the chromosomal gene may also produce an antisense sequence that inhibits transcription and/or translation of a second chromosomal gene essential for cell growth either by binding to the second chromosomal gene or by binding to mRNA transcribed from the second chromosomal gene.

In some embodiments, the chromosomal gene may inhibit cell growth via a more complicated cascade of reactions. For example, the chromosomal gene may encode an activator protein which activates expression of a second chromosomal gene which, in turn, encodes a repressor protein that inhibits expression of a third chromosomal gene encoding a protein essential for cell growth. Alternatively, the first chromosomal gene may encode an antisense inhibitor of a second chromosomal gene which, in turn, encodes a repressor protein that represses expression of a third chromosomal gene encoding a protein that inhibits cell growth. Such cascades may include more than three chromosomal genes. For example, they may include 4, 5, 6, 7 or more chromosomal genes. In all such cascades, the absence of a plasmid to inhibit the first chromosomal gene leads to the first chromosomal gene initiating a cascade reaction which ultimately results in inhibition of cell growth. Examples of suitable chromosomal genes which inhibit cell growth are provided herein.

The transformed host cell of the invention is preferably used to maintain plasmids intended for therapeutic use. Accordingly, it is preferred that the plasmid includes a cloning site for insertion of a gene of interest. Preferably, the plasmid further comprises a gene of interest. The gene of interest is preferable expressible in a mammalian cell, preferably a human cell. The gene of interest may express an RNA of interest or a protein of interest for therapeutic use. Examples of such genes of interest that may be included on the plasmid are known in the art and are provided herein The antisense sequence encoded by the plasmid may inhibit the action of the chromosomal gene by binding to the chromosomal gene itself, thereby inhibiting transcription of the gene. Alternatively, the antisense sequence encoded by the plasmid may inhibit the action of the chromosomal gene by binding to mRNA transcribed from the chromosomal gene. Depending on the nature of the chromosomal gene, binding to mRNA transcribed from the chromosomal gene may inhibit translation of the chromosomal gene or may prevent binding of an antisense sequence encoded by the chromosomal gene to its target.

In a preferred embodiment of the first aspect of the invention, a regulatory sequence is operatively linked the chromosomal gene. By "operatively linked" is meant that the regulatory sequence is linked in-frame to the chromosomal gene such that it is transcribed at the same time as the chromosomal gene. Preferably, the regulatory sequence is operatively linked upstream of the chromosomal gene. However, the regulatory region may alternatively be operatively linked downstream of the chromosomal gene. Where the regulatory sequence is operatively linked upstream of the chromosomal gene, it is preferably inserted in the ribosome binding site. Alternatively, the regulatory sequence may be inserted upstream of the ribosome binding site. The chromosomal gene or the chromosomal gene operatively linked to a regulatory gene may be under the control of a constitutive promoter or an inducible promoter. Preferably, the chromosomal gene or the chromosomal gene operatively linked to a regulatory gene is under the control of a constitutive promoter.

The antisense sequence encoded by the plasmid may inhibit the action of the chromosomal gene by binding to the regulatory sequence or by binding to mRNA transcribed from the regulatory sequence. In this embodiment of the invention, the antisense sequence encoded by the plasmid is preferably encoded by the origin replication of the plasmid.

All plasmid origins of replication produce transcribed RNA. In some cases, RNA transcribed from the origin of replication of a plasmid is used directly in the regulation of replication (e.g. plasmids R1, RK6, pT181, pMV158 and pIP501). In other cases, the transcribed RNA is translated to provide a protein required for the replication of the plasmid (e.g. pSC101, pPS10, p15A, F, R100, R453, P1, RK2, RA1, RSF10110, pColIV-K30, ColE2, ColE3, Rts1, pLS20 and pUB110), see Solar et al, 1998, Microbiol and Molec. Biol. Rev. 62: 434-363).

The invention includes transformed host cells in which the antisense sequence encoded by the plasmid is RNA transcribed from the origin of replication of any one of these plasmids. According to this embodiment, either the regulatory sequence operatively linked to the chromosomal gene or mRNA transcribed from the regulatory sequence is antisense to the RNA transcribed from the origin of replication of the plasmid. In the absence of the plasmid, the regulatory sequence operatively linked to the chromosomal gene is transcribed and/or translated, resulting in inhibition of cell growth. In the presence of a plasmid, RNA transcribed from the origin of replication inhibits the action of the chromosomal gene, thereby allowing cell growth.

According to a preferred embodiment of this aspect of the invention, the antisense sequence encoded by the plasmid is RNAI and the regulatory sequence upstream of the chromosomal gene encodes RNAII or a portion thereof. Alternatively, the antisense sequence encoded by the plasmid is RNAII and the regulatory sequence upstream of the chromosomal gene encodes RNAI or a portion thereof.

RNAI and RNAII are two overlapping RNA transcripts encoded by the origin of replication of virtually all plasmids in research and commercial use. RNAII primes the initiation of plasmid DNA synthesis, allowing autonomous plasmid replication to take place in E. coli. RNAI is the antisense inhibitor of RNAII and prevents excess plasmid replication to ensure that plasmid copy number does not exceed a number that can be supported by the host cell. It has now been found that this antisense mechanism can be exploited to promote plasmid maintenance in a transformed host cell.

According to this embodiment, the invention provides a transformed host cell containing
   i) an RNAII coding region or a portion thereof operatively linked to a chromosomal gene, wherein the chromosomal gene inhibits cell growth; and
   ii) a plasmid comprising an RNAI coding region or a portion thereof, wherein RNAI transcribed from said RNAI coding region or portion thereof binds to RNAII transcribed from said RNAII coding region or portion thereof, inhibiting the action of the chromosomal gene and thereby permitting cell growth.

The RNAII coding region or portion thereof operatively linked to the chromosomal gene is transcribed, resulting in an RNAII-chromosomal gene mRNA. In the absence of the plasmid encoding RNAI, cell growth is inhibited. Cell growth may be inhibited by the RNAII-chromosomal gene mRNA binding to a second chromosomal gene essential for cell growth or to mRNA transcribed from such a second chromosomal gene. Alternatively, the RNAII-chromosomal gene may be translated and cell growth may be inhibited as a result of a toxic protein encoded by the chromosomal gene or as a result of a repressor protein encoded by the chromosomal gene inhibiting a second chromosomal gene essential for cell growth. When the plasmid is present, RNAI transcribed from the plasmid binds to RNAII in the RNAII-chromosomal gene mRNA, preventing the chromosomal gene from inhibiting cell growth.

The invention further provides a transformed host cell containing
  i) an RNAI coding region or a portion thereof operatively linked to a chromosomal gene, wherein the chromosomal gene inhibits cell growth; and
  ii) a plasmid comprising an RNAII coding region or a portion thereof, wherein RNAII transcribed from said RNAII coding region or portion thereof binds to RNAI transcribed from said RNAI coding region or portion thereof, inhibiting the action of the chromosomal gene and thereby permitting cell growth.

The RNAI coding region or portion thereof operatively linked to the chromosomal gene is transcribed, resulting in an RNAI-chromosomal gene mRNA. In the absence of the plasmid encoding RNAII, cell growth is inhibited. Cell growth may be inhibited by the RNAI-chromosomal gene mRNA binding to a second chromosomal gene essential for cell growth or to mRNA transcribed from such a second chromosomal gene. Alternatively, the RNAI-chromosomal gene may be translated and cell growth may be inhibited as a result of a toxic protein encoded by the chromosomal gene or as a result of a repressor protein encoded by the chromosomal gene inhibiting a second chromosomal gene essential for cell growth. When the plasmid is present, RNAII transcribed from the plasmid binds to RNAI in the RNAI-chromosomal gene mRNA, preventing the chromosomal gene from inhibiting cell growth.

All plasmids produce RNA transcribed from the origin of replication and the majority of commercially available plasmids contain an origin of replication comprising an RNAI coding region and an RNAII coding region. Unlike the system disclosed in EP 0851932 where plasmid maintenance depends on cloning a lac operator system into the plasmids used, the current invention enables maintenance of any commercially available plasmids comprising any origin of replication in transformed host cells and selection of host cells maintaining these plasmids without the need to clone any additional sequences into the plasmids. This has the advantage that plasmid size is reduced, increasing the effective dose of plasmid in DNA vaccine and gene therapy applications. The removal of unnecessary bacterial DNA also reduces the risk of immune response to CpG dinucleotides.

In addition, plasmid maintenance can be achieved without the antibiotic selection. The plasmids do not therefore require the presence of an antibiotic resistance gene. The absence of an antibiotic resistance gene on the plasmid has a number of advantages, particularly in situations where the plasmid, or a product encoded by the plasmid, is intended for therapeutic use. Firstly, the absence of an antibiotic resistance gene on the plasmid removes the risk of antibiotic resistance gene transfer to organisms in the environment, including potential pathogens. It also prevents the contamination of plasmids isolated from the cells with residual antibiotics used for plasmid selection and thus removes the requirement to test the plasmids for the presence of residual antibiotics and the risk of antibiotic resistance genes causing detrimental effects in patient cells. The fact that selection is not dependent on antibiotic resistance avoids the problem of lack of plasmid selection pressure due to antibiotic breakdown during culture.

Plasmids for use in the invention include plasmids in which RNA transcribed from the origin of replication is used directly in the regulation of replication such as plasmids R1, RK6, pT181, pMV158 and pIP501 and plasmid in which RNA transcribed from the origin of replication is translated to provide a protein required for the replication of the plasmid, such as pSC101, pPS10, p15A, F, R100, R453, P1, RK2, RA1, RSF1010, pColIV-K30, ColE2, ColE3, Rts1, pLS20 and pUB110. Preferably, plasmids for use in the invention comprise an origin of replication comprising an RNAI coding region and an RNAII coding region. Plasmids comprising an origin of replication comprising an RNAI coding region and an RNAII coding region include plasmids comprising a ColE1 type ori, such as the colE1ori and pMB1ori.

The RNAII coding region, RNAI coding region or portion thereof operatively linked to a chromosomal gene which inhibits cell growth may be under the control of a constitutive promoter or an inducible promoter. Preferably, the RNAII coding region, RNAI coding region or portion thereof operatively linked to a chromosomal gene which inhibits cell growth is under the control of a constitutive promoter Suitable constitutive promoters are known in the art and include, for example, promoters containing the −35 and −10 sequences from *E. coli* promoter such as the trc promoter.

According to a second aspect of the invention, there is provided a host cell comprising a chromosomal gene which inhibits cell growth operatively linked to a regulatory sequence located upstream of the chromosomal gene, wherein the regulatory sequence comprises a sequence which is antisense to the sequence of an RNA transcribed from a plasmid origin of replication or wherein the regulatory sequence encodes an RNA sequence which is antisense to the sequence of an RNA transcribed from a plasmid origin of replication. The nature of the regulatory sequence will depend on the identity of the plasmid with which the host cell is intended to be transformed. Examples of suitable plasmid origins of replication are provided above. It will be apparent to the skilled person how to design a regulatory sequence which is antisense to RNA transcribed from these origins of replication.

Preferably, the regulatory sequence comprises an RNAI coding region or a portion thereof, or an RNAII coding region or a portion thereof. The RNAII coding region, RNAI coding region or portion thereof operatively linked to a chromosomal gene which inhibits cell growth may be under the control of a constitutive promoter or an inducible promoter. Preferably, the RNAII coding region, RNAI coding region or portion thereof operatively linked to a chromosomal gene which inhibits cell growth is under the control of a constitutive promoter Suitable constitutive promoters are known in the art and include, for example, promoters containing the −35 and −10 sequences from *E. coli* promoter such as the trc promoter.

The host cell according to this second aspect of the invention may be transformed with a plasmid comprising an RNAI coding region and an RNAII coding region to produce a transformed host cell according to the first aspect of the invention.

The host cell and transformed host cells of the invention may be in culture in vitro. Examples of suitable host cells are provided herein.

According to a third aspect of the invention. there is provided a method of maintaining a plasmid in a host cell in vitro comprising the step of culturing a transformed host cell as described above under conditions sufficient to permit said cell to grow. This method enables plasmid maintenance and selection to be carried out in the absence of antibiotic resistance, making it particularly suitable for the production of plasmid DNA or recombinant proteins for therapeutic applications. According to a fourth aspect of the invention, there is provided a method of producing plasmid DNA comprising carrying out the method of the third aspect of the invention and isolating the plasmid DNA. According to a fifth aspect of the invention, there is provided a method of producing a recombinant protein comprising culturing a transformed host cell comprising a plasmid encoding a protein of interest according to the method of the third aspect of the invention and isolating the protein from the cell.

The transformed host cells and host cells of the invention may themselves have therapeutic applications. According to a sixth aspect of the invention, there is provided a transformed host cell according to a first aspect of the invention of the invention for use in therapy.

According to a seventh aspect of the invention, there is provided a pharmaceutical composition comprising a transformed host cell according to a first aspect of the invention together with a pharmaceutically acceptable excipient, diluent or buffer, such as are well-known to those of skill in the relevant art. According to one embodiment of this aspect, the pharmaceutical composition is a vaccine composition. The vaccine composition may comprise one or more adjuvants in additional to the excipient, diluent or buffer.

According to an eighth aspect of the invention, there is provided the use of a transformed host cell according to a first aspect of the invention in the manufacture of a medicament. Preferably, the transformed host cell may be used as a gene delivery system. For example, the transformed host cell may be used to deliver a gene of interest on the plasmid for gene therapy purposes. The transformed cell may also be used to deliver a gene of interest on the plasmid, the transcription product of which has a therapeutic effect, such as an antisense oligonucleotide or to deliver a gene of interest which encodes a protein which has a therapeutic effect.

Alternatively, the transformed host cell may be used to deliver an immunogen. According to this embodiment, a gene of interest on the plasmid may encode one or more antigens which elicit an immune response. The skilled person will be aware of genes of interest which encode antigens which elicit an immune response and which may be included in the plasmid in the transformed cell of the invention.

According to a ninth aspect of the invention, there is provided a method of treatment comprising administering to a patient the transformed host cells described above, or a composition comprising them. In particular, there is provided a method of delivering a gene of interest to a patient comprising administering to the patient the transformed host cells described above or a composition comprising them. As described above, a gene of interest on the plasmid in the transformed host cell may itself be useful for gene therapy purposes or the transcription or transcription and translation product of the gene of interest may have therapeutic properties.

According to a tenth aspect of the invention, there is provided a method of immunising a patient against a disease caused by a pathogen comprising administering to the patient the transformed host cells described above or a composition comprising them, wherein a gene of interest found on the plasmid in the cells encodes an antigen which induces an immune response against the pathogen. The antigen may be expressed in the cells before they are administered to the patient or the cells containing the plasmid may be administered to the patient with the antigen being expressed in the patient after administration depending of on the nature of the cells and of the promoter controlling the expression of the gene of interest. Preferably, the cell is a bacterial cell, as described above, and the gene of interest is functionally linked to either a bacterial promoter or a eukaryotic promoter.

According to an eleventh aspect of the invention, there is provided a method of maintaining a plasmid in a host cell in vivo comprising supplying a transformed host cell according to a first aspect of the invention to a recipient organism. Preferably, the recipient organism is a mammal, preferably a human. According to this aspect of the invention, the chromosomal gene preferably inhibits cell growth in vivo such that only host cells which maintain the plasmid survive in vivo in the recipient organism. For example, the chromosomal gene may encode a repressor protein for a second chromosomal gene which encodes a protein which is essential to the integrity of the cell.

Examples of suitable plasmid, borne genes of interest, host cells and of chromosomal genes which inhibit cell growth for use in the invention, as well as information on the medical applications of the transformed host cells of the invention are provided below.

Chromosomal Genes

The chromosomal gene included in the host cells and transformed host cells of the invention may be any gene which inhibits growth.

Chromosomal genes which inhibit growth directly

Preferred chromosomal genes which inhibit cell growth directly include genes encoding toxins. Examples of genes encoding toxins which may be used in the invention include the sacB gene from *B. subtilis*, CcdB encoded by the ccdb in the *E. coli* F plasmid, the Kid protein encoded by the parD gene from plasmid RK2, restriction endonuclease genes and antibiotic genes.

Chromosomal genes which inhibit growth indirectly by inhibiting genes essential for growth Preferred chromosomal genes which inhibit growth indirectly include chromosomal genes encoding a protein repressor which inhibit a second chromosomal gene essential for cell growth and chromosomal genes encoding an antisense sequence which inhibits a second chromosomal gene essential for cell growth. In one embodiment of the invention, the second chromosomal gene is conditionally essential for cell growth.

Where the chromosomal gene encodes a protein repressor, the second chromosomal gene is preferably operatively linked to an operator and promoter which is conventionally inhibited by that repressor.

For example, if the chromosomal gene encodes the protein repressor LacI, the second chromosomal gene essential for cell growth is preferably operatively linked to a lac operator and promoter. The *E. coli* lac repressor is described in "The Lactose Operon", J. Beckwith, in *Escherichia coli* and *Salmonella typhimurium*, Eds., J. L. Ingraham et al., 1987 Amer. Soc. Micro., pp. 1444-1452, and Dickson et al., 1975, Science 187:27-35. The lac operon is regulated as follows. Under non-inducing conditions (such as growth on glucose) LacI binds to the operator of the lac operon and prevents transcription of b-galactosidase (LacZ), lactose permease (LacY) and a transacetylase (LacA). Under inducing conditions (such as growth on lactose or addition of IPTG, a non-metabolizable analogue) the repressor no longer binds to the operator and transcription occurs. The expression of the operon is easily detected by assay for b-galactosidase.

Other repressor systems useful according to the present invention include the tet repressor system for use in regulating gene activity in eukaryotic cells (Gossen et al., (1994) Current Opinions in Biotechnology, 5, 516-520). The tet repressor system has been used in yeast, dictiostelium, plant cells and tobacco plants. A further repressor system useful according to the present invention is the ArgRNV repressor system (Burke et al., (1994) Mol. Microbiol. 13, 609-618). The ArgR repressor normally only binds to its operator in the presence of Arginine. However, the mutant ArgRNV repressor binds to the operator in the absence of arginine and remains bound in the presence of arginine and has a transdominant effect. An idealised ArgR binding site (operator) having two symmetrical Arg boxes, can be engineered into the plasmid of interest to enable the titration of ArgRNV away from an essential gene the expression of which is controlled by the ArgR binding site.

The *E. coli* trp repressor also is useful according to the invention (see "The tryptophan Operon", Yanof sky and Crawford, in *Escherichia coli* and *Salmonella typhimurium*, mEds., J. L. Ingraham et al., 1987, Amer. Soc. Micro., pp. 1453-1472). The trp repressor is present at about 50 copies/cell, and requires the presence of tryptophan in the fermentation medium as an inducer of repressor binding.

The *E. coli* galR repressor is useful according to the invention (see "The Galactose Operon", S. Adhya, in *Escherichia coli* and *Salmonella typhimurium*, Eds., J. L. Ingraham et al., 1987, Amer. Soc. Micro., pp. 1503-1512).

The *E. coli* araC repressor is also useful according to the invention (see "The L-Arabinose Operon", R. Schlief, In *Escherichia coli* and *Salmonella typhimurium*, Eds., J. L. Ingraham et al., 1987, Amer. Soc. Micro., pp. 1473-1481; Dunn et al., 1984, Proc. Nat. Aca. Sci. 81;5017-5020). The araC repressor has increased binding affinity in the presence of arabinose.

Finally, the A repressor is useful according to the invention (Introduction to Lambda Phages, in Current Protocols in Molecular Biology, Eds. Ausubel, et al., 1994, Section III, Unit 1.9; Hochschild et al., 1986, Cell 47(5);807-816).

The second chromosomal gene essential for cell growth may be a gene encoding products related to the biosynthesis of cell metabolites, a gene whose products are involved in carbon metabolism or a gene encoding the biosynthesis or regulation of macromolecules, e.g., a gene essential for DNA and/or RNA synthesis and replication functions of the host cell.

Certain genes encoding enzymes involved with the supply of cell components, in particular the supply of cell wall precursors, are essential for host cell growth and are useful according to the invention. For example, the bacterial cell wall contains meso-diamiopimelic acid (DAP), and an inability to synthesize this component results in cell lysis. Genes in the DAP biosynthetic pathway, namely dapA, dapB, dapC, dapD and dapE genes may therefore be used as the second chromosomal gene essential for cell growth which is inhibited by the first chromosomal gene. dapA and dapB have been cloned and sequenced, and dapB is available as a single cistron (Richaud et al., J. Bacteriol. 166:297-300, 1986; Bouvier et al., J. Biol. Chem. 259:14829-14834, 1984).

The genes involved in the biosynthesis of other cell wall components, such as D-alanine biosynthesis, are also useful according to the invention (Walsh, 1989, J. Biol. Chem.264 (5):2393-2396).

Genes involved in fatty acid biosynthesis are also useful according to the invention. One example is fabA, which encodes 3-hydroxydecanoyl-ACP dehydrase, responsible for the introduction of a double bond into the growing fatty acid chain at the point where unsaturated and saturated fatty acid biosynthesis diverges (Cronan Jr. J. E. and Rock. C. O. (1987)). Biosynthesis of membrane lipids. In '*Escherichia coli* and *Salmonella typhimurium*: cellular and molecular biology'. Neidhardt. F. C. (ed.) American Society of Microbiology, Washington D.C.). The enzyme is present at relatively high concentration, and fabA mutants lyse unless supplemented with an unsaturated fatty acid.

Alternatively, the second chromosomal gene essential for cell growth may be a gene involved with the utilization of carbon sources. Specifically, the second chromosomal gene may comprise the genes of the lactose operon such that, in conditions where lactose is the sole carbon source, only cells which maintain the plasmid and in which the genes of the lac operon are expressed, can survive. Other modifications will be apparent to one of skill in the art.

Glutamine synthetase is an essential gene for eukaryotic cells such as the NSO myeloma cell line (Bebbington et al., (1992) Bio/Technology 10, 169-175) and is preferably used as the second chromosomal gene when the host cell is a eukaryotic cell.

The second chromosomal gene may also be an essential gene encoding DNA and/or RNA synthesis or replication proteins of the host cell. Examples of such genes with respect to these essential functions in bacteria such as *E. coli* and *Salmonella* are provided in McMacken et al. (in *Escherichia coli* and *Salmonella typhimurium*, Cellular and Molecular Biology, Ed. Neidhardt et al., Amer. Soc. Micro., Wash. D.C., 1987, pp. 564-612), and include but are not limited to the following genes: dnaA, dnaB, dnaC, ssb, dnaG, polC (dnaE), dnaQ (mutD) dnaN, dnaZX, gyrA, gyrB, polA, lig, dnaT, rpoA, rpoB, rpoC, and rpoD.

Although not preferred, the second chromosomal gene may be an antibiotic resistance gene such that transformation of the strain with plasmid allows growth in the presence of that antibiotic.

For transformed host cells for use in medical applications, depending on the route of administration, a number of factors in the local environment may exert selective pressure. Where an ability to resist such pressure is linked to an identified gene, then this may be used as a selectable marker. For instance, for cells, especially bacterial cells to be administered orally, resistance to the low pH of the stomach contents constitutes a significant selective advantage. Among the genes shown to be associated with this are the uvrA gene of *Streptococcus mutans* (Hanna et al, 2001 J Bacteriol 183: 5964), the gadA, B and C genes of *E. coli* (Castanie-Comet and Foster, 2001, Microbiology 147: 709), the rpoS, fur, atp and atbR genes of *Salmonella typhimurium* (Baik et al, 1996 Microbiology 142: 3195), the lepA, Frasel, czcA, uvrA, atpF'and aldo-keto reductase genes of *Helicobacter pylori* (Bijlsma et al, 2000, J Infect Dis 182: 1566) and the genes encoding the $F_0F_1$ ATPase of *Listeria monocytogenes* (Cotter et al 2000 Int J Food Microbiol 60: 137).

Genes conferring intracellular survival (for instance SvpA in *Listeria monocytogenes* Borezee et al, 2001, Microbiology 147:2913) or resistance to particular intracellular locations such as lysosomes might also be useful in appropriate host cells.

Preferred genes which inhibit cell growth indirectly also include chromosomal genes encoding an antisense sequence that inhibits a second chromosomal gene essential for cell growth either by binding to the second chromosomal gene or by binding to mRNA transcribed from the second chromosomal gene.

An antisense sequence is one that is substantially complementary to its target sequence and has the ability to specifically hybridize to that target sequence. Since the antisense sequence may act by binding either directly to a second chromosomal gene essential for cell growth or to mRNA transcribed from that second chromosomal gene, the target sequence may be the sequence of either the coding strand or the non-coding strand of the second chromosomal gene, or a portion thereof. Methods of preparing antisense sequences which have the ability to specifically hybridise to target sequences will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991).

Preferably, the antisense sequences hybridise to the target sequences under stringent conditions. High stringency hybridisation conditions are defined as overnight incubation at 42° C. in a solution comprising 50% formamide, 5×SSC (150 mM NaCl, 15 mM trisodium citrate), 50 mM sodium phosphate (pH7.6), 5× Denhardts solution, 10% dextran sulphate, and 20 microgram/ml denatured, sheared salmon sperm DNA, followed by washing the filters in 0.1×SSC at approximately 65° C.

As indicated previously, a first chromosomal gene may inhibit cell growth by initiating a cascade of reactions involving a number of genes which ultimately result in inhibition of a gene essential for cell growth or activation of a gene which inhibits cell growth. For example, the first chromosomal gene may encode repressor protein which inhibits a second chromosomal gene encoding an activator which would otherwise activate a third chromosomal gene essential for cell growth. Alternatively, the first chromosomal gene may encode a repressor protein which inhibits a second chromosomal gene encoding an antisense sequence which would otherwise inhibit a third chromosomal gene that inhibits cell growth. It will be apparent to the skilled person that these are merely examples of the many cascades of genes which would satisfy the requirements of the invention.

Production of Modified Host Cells

The chromosomal gene which inhibits cell growth may be a gene that is naturally present in the host cell genome or may be an exogenous gene.

Where the antisense sequence encoded by the plasmid inhibits the chromosomal gene by binding to a regulatory sequence operatively linked to the chromosomal gene, the chromosomal gene may be a naturally-occurring gene which has been operatively linked to an exogenous regulatory sequence. For example, the sequences which normally control expression of a naturally-occurring toxin gene may be removed and the toxin gene instead operatively linked to an exogenous RNAI coding sequence under the control of a constitutive promoter. Similarly, the sequences which normally control the expression of a naturally occurring repressor protein may be removed and the repressor protein gene instead operatively linked to an exogenous RNAII coding sequence under the control of a constitutive promoter or of an inducible promoter. Hence, in example 2 herein, a naturally occurring repressor gene, lacI, is operatively linked to an RNAII coding region.

Alternatively, both the regulatory sequence and the chromosomal gene may be exogenous, as is the case when the regulatory sequence is an RNAI or RNAII coding sequence and the chromosomal gene encodes an antisense sequence that inhibits a second chromosomal gene essential for cell growth.

If a second chromosomal gene essential for cell growth is present, it may also be either a naturally-occurring gene or an exogenous gene.

The chromosomal gene which inhibits cell growth may be present in the genome of the cells in multiple copies, particularly where the host cell is a eukaryotic host cell.

It will be apparent to the person skilled in the art how to manipulate a cell in order to produce a host cell suitable for use in the invention.

Host Cells

The invention is applicable to all cell types including animal cells, such as mammalian and insect cells, plant cells, fungi (such as yeast), bacteria and archaea.

Where the host cell is a bacterial cell, it may be a gram negative bacterial cell or a gram positive bacterial cell. Where the cell is a gram negative bacterial cell, it is preferably an *E. coli* cell or a *Salmonella* cell. Where the cell is a gram positive bacterial cell, it is preferably a *Bacillus, Streptomyces, Lactobacillus* or *Lactococcus* cell.

Particularly useful are attenuated host cells that have been attenuated so as to be acceptably free of side-effects free for therapeutic use in recipient organisms. Depending on the specificity of the cell, it may be suitable for veterinary or human therapeutic use.

Among the attenuated bacteria available are the following:

*Salmonella typhimurium* including strains SL3261 (aroA mutant, Titball et al, 1997, Infection and Immunity 65: 1926, Titball et al, 1995, Infection and Immunity 63: 563), VNP20009 (purI and msbB mutant, Toso et al, 2002, J Clin Oncol 20: 142);

*Salmonella typhi* including strains CVD 908-htrA, $\chi$4073, $\chi$4632, Ty800, CVD 909 and CVD 915 (Galen et al, 1999, Infect. Immun. 67: 6424-6433; Morona et al, 1991, Gene 107: 139-144; Tacket et al, 1997, Infect. Immun. 65: 3381-3385; Garmory et al, 2002, FEMS Microbiology Reviews 26: 339-353);

*Salmonella gallinarum* including strain 9R (for avian vaccination, Feberwee et al, 2001, Avian Dis 45: 1024);

*Escherichia coli* including aroA, cnfI and OMP mutants (Rippere-Lampe et al, 2001, Infect Immunol 69: 3954);

*Shigella flexneri* including strain *S. flexneri* 2a guaBA (Altboum et al, 2001, Infect Immunol 69:3150);

*Vibrio cholerae* including strain Peru2 (Ryan et al, 2000, Infect. Immun. 68: 221-226);

*Listeria monocytogenes* including PrfA and SvpA mutants (Sheehan et al, 1996, Mol Microbiol 20: 785; Borezee et al, 2001, Microbiology 747:2913);

*Brucella abortus* including strain RB51 (Vemulapalli et al, 2000, Infect Immunol 68:3290);

*Mycobacterium bovis* including the strain Calmette-Guerin (BCG); and

*Mycobacterium tuberculosis.*

Plasmid-Borne Genes Useful According to the Invention

A gene of interest borne on the plasmid in the transformed host cells of the invention may be any gene. The gene may be one which has a therapeutic effect when delivered to a recipient organism. For example, it may be desirable to deliver the gene to a recipient organism for gene therapy purposes.

Alternatively, it may be desirable to deliver a gene to a recipient organism because the transcription product or the transcription and translation product of the gene has a therapeutic effect. For example, the transcription product of a gene of interest may be an antisense oligonucleotide or the gene of interest may encode an antigen which has a therapeutic effect. In particular, a gene of interest may encode one or more antigens which elicit an immune response in a recipient organism. An example of genes of interest which may be included in the plasmid to induce an immune response in the recipient organism are the cafI, cafIA and cafIM genes of the caf operon.

Where it is desired that the gene of interest be transcribed or transcribed and translated, it is preferably functionally associated with a promoter. Preferably, the promoter is a eukaryotic promoter or a bacterial promoter. The choice of the promoter functionally associated with the gene of interest and the choice of the host cell determines whether the gene of interest is transcribed, or transcribed and translated, in the host cell prior to administration to a recipient organism or only after administration to a recipient organism.

In some cases, it may be desirable to deliver host cells already expressing a gene of interest, in which case, the promoter functionally associated with the gene of interest will be chosen such that it is operational in the host cell and promotes transcription and translation of the gene of interest in the host cell. For example, where the host cell is a bacterial cell, the promoter functionally associated with the gene of interest in this situation may be a bacterial promoter.

In other cases, it may be desirable to deliver host cells comprising the plasmid comprising the gene of interest to a recipient organism but to delay expression of the gene of interest until after delivery of the cells to the recipient organism. For example, where the host cell is a bacterial cell, the promoter functionally associated with the gene of interest in this situation may be a eukaryotic promoter which will not promote transcription and translation of the gene of interest in the host cell but will do so following administration to a recipient organism.

Methods of Vaccination Useful According to the Invention

It is envisaged that vaccination with transformed host cells according to the invention might be by any of a number of routes of administration. For *Mycobacterium*, for instance the usual route is by intradermal or subcutaneous injection. For enteric bacteria such as *Salmonella, Shigella* or *E coli*, oral administration (particularly of acid-resistant transformants) or rectal administration is preferable. In some circumstances, mucosal, intravenous or intraperitoneal administration might be preferred.

Administration for Other In Vivo Applications

It is envisaged that a number of methods of administration for non-vaccination applications might be used.

In addition to the enteral and parenteral routes of administration used for vaccination, non-vaccine application might require other procedures. Amongst these are the use of implantable permeable containers in which cells according to the invention are contained.

BRIEF DESCRIPTION OF THE FIGURES

FIG. 2: Example of genome of host cell for use in Repressor oriSELECT. The genome of a host cell contains an RNAII coding region linked to a repressor gene cistron, both of which are under the control of a constitutive RNAII promoter. The genome further contains an essential gene under the control of an inducible promoter. In the absence of a plasmid, the repressor protein is expressed and represses the essential gene, inhibiting cell growth. Binding of plasmid-generated RNAI to the RNAII transcript of the RNAII-repressor mRNA fusion blocks translation of the repressor protein, allowing expression of the essential gene and cell growth.

FIG. 3: Example of genome of host cell for use in Toxin gene oriSELECT. The genome contains a sacB gene, encoding levansucrase from *Bacillus subtilis* (Link et al, 1997 *J. Bacteriol.* 179: 6228-6237), placed downstream of RNAII. In the presence of sucrose, sacB synthesises a toxic product and the cell is killed in the presence of sucrose unless a plasmid expressing RNAI which blocks translation of the toxin gene mRNA is present.

FIG. 4: Example of genome of host cell for use in Antisense oriSELECT. The host cell genome contains a gene which is essential for cell growth and an RNAII coding region linked to a gene which is antisense to the gene essential for cell growth. In the absence of a plasmid, the antisense RNA will bind to the essential gene mRNA, thereby preventing translation of the essential gene and cell growth. When the cell is transformed with a plasmid providing RNAI, RNAI will bind to the RNAII-antisense RNA and prevent it from binding to the essential gene mRNA, allowing cell growth.

FIG. 5: Amplification of the 5' end of RNAII from pUC18 by PCR. Positions of RNAI and RNAII transcripts are shown as are positions of primers used to amplify 5' end of RNA II prior to its insertion upstream of the gene encoding the repressor lacI for insertion into a host cell genome for use in Repressor oriSELECT.

FIG. 8: Further example of genome of host cell for use in Repressor oriSELECT. The genome of a host cell contains an RNAII coding region linked to a repressor gene cistron (lacI), both of which are under the control of a constitutive promoter based on the –10 and –35 sequences and spacing found in the *E. coli* trc promoter. The genome further contains an essential gene under the control of an inducible promoter (not shown). In the absence of a plasmid, the repressor protein is expressed and represses the essential gene, inhibiting cell growth. Binding of plasmid-generated RNAI to the RNAII transcript of the RNAII-repressor mRNA fusion blocks translation of the repressor protein, allowing expression of the essential gene and cell growth.

The invention will now be described in more detail by way of example with reference to systems of plasmid maintenance employing a plasmid origin of replication as a selectable marker. It will be appreciated that modifications may be made to the systems described in the Examples.

EXAMPLES

Figure 1:
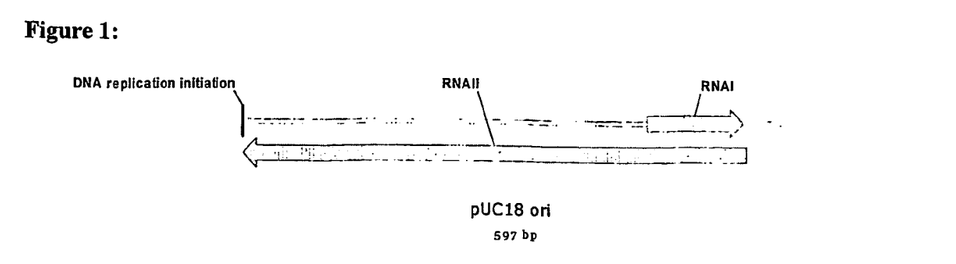
FIG. 1: Diagram of pUC18 ori showing location of RNAI and RNAII transcripts. RNAII primes the initiation of plasmid DNA synthesis, and RNAI is the antisense inhibitor of RNAII.

The invention allows the selection and maintenance of plasmids using only the origin of replication (pMB1 or ColEI ori) as the selectable marker and is referred to herein as oriSELECT. As shown in FIG. 1, these ColEI-compatible oris encode two overlapping RNA transcripts: RNAII primes the initiation of plasmid DNA synthesis, and RNAI is the antisense inhibitor of RNAII (Scott et al, 1984, *Microbiol. Rev.* 48: 1-23; Chan et al, 1985 *J. Biol. Chem.* 260: 8925-8935). Virtually all plasmids in research or commercial use rely on these oris for autonomous replication in *E. coli*.

The invention may involve the construction of genetically-modified strains of *E. coli* in which the genome has been modified to contain an region encoding RNAII linked to an inhibitory genetic element in an operon. Binding of plasmid-generated RNAI to the RNAII-mRNA fusion prevents transcription of the inhibitory gene mRNA, thus allowing cell survival and growth. Three proposed mechanisms of this system of plasmid maintenance are described below.

Example 1

Repressor oriSELECT

Figure 2:
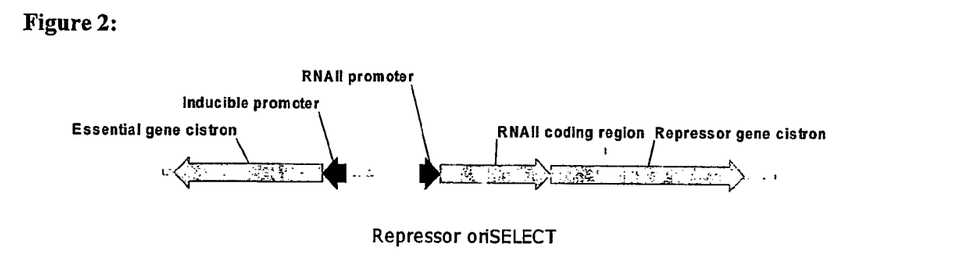
Figure 8:
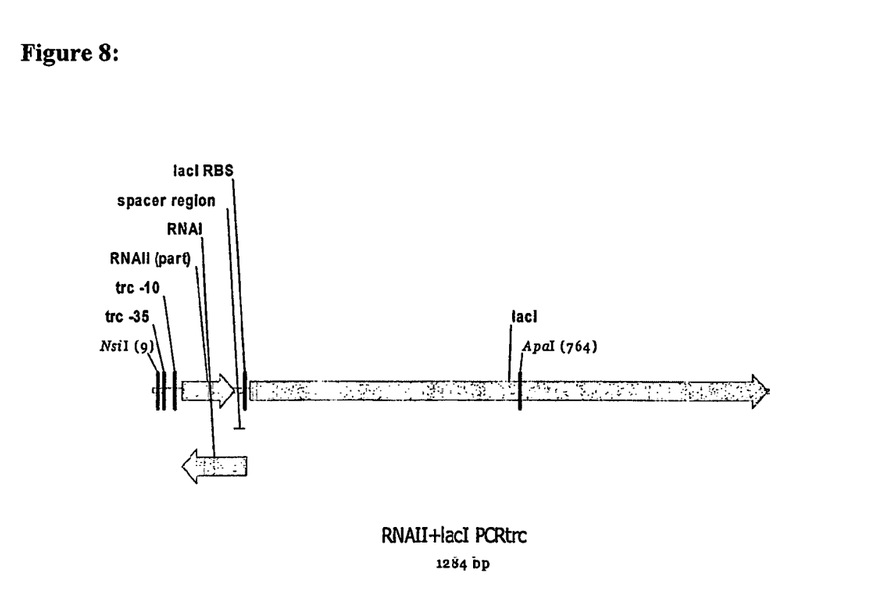

As shown in FIG. 2, the genome of a host cell for use in repressor oriSELECT contains an RNAII coding region linked to a repressor gene cistron, both of which are under the control of a constitutive RNAII promoter. The RNAII coding region linked to a repressor cistron may also be under the control of an alternative constitutive promoter, such as a promoter based on the *E. coli* −10 and −35 sequences and spacing found in the Trc promoter, as shown in FIG. 8. The host cell genome also contains a gene essential for cell growth under the control of an inducible promoter (not shown in FIG. 8).

In the absence of a plasmid, the repressor protein is expressed and represses the essential gene by binding to the operator/promoter controlling expression of the essential gene, inhibiting cell growth. Binding of plasmid-generated RNAI to the RNAII transcript in the RNAII-repressor mRNA fusion blocks translation of the repressor, allowing expression of the essential gene and thus cell growth.

To construct this host cell for use in Repressor oriSELECT, the essential gene, such as dapD (Richaud et al, 1984, *J. Biol. Chem.* 259: 14824-14828) or fabA (Cronan et al, 1987, Biosynthesis of membrane lipids. In '*Escherichia coli* and *Salmonella typhimurium: cellular and molecular biology*', Neidhardt, F. C. (ed.). American Society of Microbiology, Washington D.C.), is deleted from the chromosome of a bacterial strain, placed under the control of an inducible promoter (e.g. Plac) and inserted back into the chromosome. The gene encoding the repressor associated with the inducible promoter, in this case lacI, is deleted from the chromosome. This repressor gene is placed in an operon downstream of the region encoding part of RNAII, with the constitutive RNAII promoter (or any other constitutive promoter, for example a promoter based on the *E. coli* −10 and −35 sequences and spacing found in the trc promoter) driving transcription of both. The 3' end of the RNAII coding region is modified to incorporate the ribosome-binding site of the repressor, such that it will be overlapped and blocked by RNAI. In some cases, expression of the LacI repressor protein may be increased by increasing the distance between the 3' end of the RNAII coding region and the lac ribosome binding site. This construct is inserted into the chromosome.

The cell will now produce the repressor constitutively. The repressor protein will bind to the chromosomal operator controlling the essential gene, thereby preventing cell growth. When the cell is transformed with a plasmid containing a ColEI-compatible ori, RNAI will bind to RNAII and block translation of the downstream repressor gene, allowing cell growth.

If the chromosomal essential gene has its own associated repressor, this repressor (minus its promoter) can be engineered into an operon downstream of RNAII and this operon inserted into the bacterial chromosome to replace the wild-type repressor.

The essential gene may be a conditionally essential exogenous gene (e.g. an antibiotic resistance gene).

If the essential exogenous gene is inducible and has its own associated exogenous repressor, this repressor gene can be engineered into an operon downstream of RNAII and this operon inserted into the bacterial chromosome.

Example 2

Toxin Gene oriSELECT

Figure 3:
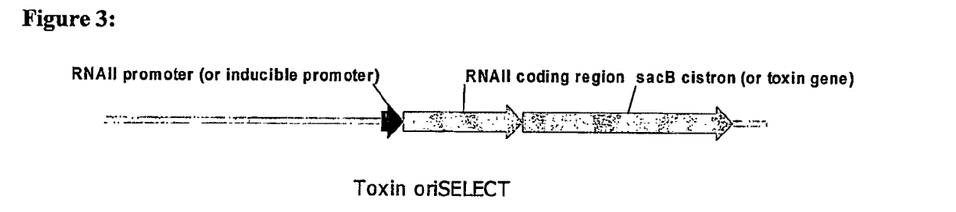

As shown in FIG. 3, the genome of a host cell for use in toxin gene oriSELECT contains a sacB gene, encoding levansucrase from *Bacillus subtilis* (Link et al, 1997 *J. Bacteriol.* 179: 6228-6237), placed downstream of RNAII. In the presence of sucrose, sacB synthesises a toxic product and the cell is killed unless a plasmid expressing RNAI is introduced. Another toxic gene regulated by an inducible promoter may be fused to the RNAII coding region instead of sacB.

A construct is engineered with an operon consisting of the RNAII coding region and a downstream gene encoding sacB. The 3' end of the RNAII coding region is modified to incorporate the ribosome-binding site of sacB. A constitutive RNAII promoter drives gene expression. When this is inserted into the bacterial chromosome, the cell can grow in the absence of sucrose, but when sucrose is added, the toxin is produced and the cell dies. When the cell is transformed with a plasmid containing a ColEI-compatible ori, RNAI will bind to the RNAII-toxin gene mRNA and block translation, allowing cell growth in the presence of sucrose.

A temperature-sensitive or chemically-induced promoter may be used to drive expression of the RNAII-toxin gene fusion. At the permissive temperature or in the presence of an inducer, the cell is killed unless a plasmid expressing RNAI is introduced.

Example 3

Double antisense oriSELECT

Figure 4:
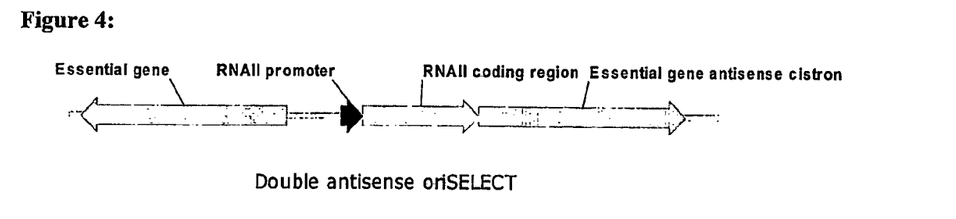

As shown in FIG. 4, in double antisense oriSELECT, the host cell genome contains a gene which is essential for cell growth and an RNAII coding region linked to a gene which is antisense to the gene essential for cell growth.

An antisense version of an essential gene (e.g. dapD or fabA) is placed in an operon downstream of the region encoding RNAII, with the constitutive RNAII promoter driving transcription of both. The 3' end of the RNAI coding region may be modified to incorporate part of the essential gene antisense transcript, such that it will be partially overlapped by RNAII. This construct is inserted into the bacterial chromosome.

The cell will now produce the RNAII and antisense RNA constitutively. The antisense RNA will bind to the essential gene mRNA, thereby preventing translation of the essential gene and cell growth.

When the cell is transformed with a plasmid containing a ColEI-compatible ori, RNAI will bind to the RNAII-antisense RNA and prevent it from binding to the essential gene mRNA, allowing cell growth.

Example 4

Creation of Repressor oriSELECT Strain

The ORT strains DH1lackan (Willians et al, 1998), DH1lacdapD and DH1lacP2dapD (Cranenburgh et al, 2001, *Nucleic Acid Res.* 29: e26) may converted to oriSELECT strains by the integration of the RNAII-lacI operon into (and thus replacing) the chromosomal lacI repressor gene. A single plasmid built based on the pKO3 integration system (Link et al, 1997 *J. Bacteriol.* 179: 6228-6237), is used to replace wild-type lacI with RNAII-lacI in all ORT strains as follows.

1. Amplify part of the chromosomal lac operon surrounding lacI by PCR and clone;
2. Engineer an operon consisting of the RNAII coding region inserted upstream of the lacI repressor gene, replacing its natural promoter. The lacI ribosome binding site should be located such that on the mRNA, it is blocked by the binding of antisense RNAII.
3. Clone the RNAII-lacI operon locus into the integration plasmid pKO3.
4. Integrate RNAII-lacI operon locus into the wild-type lac operon locus of DH1lackan, DH1lacdapD and DH1lacP2dapD to produce oriSELECT strains.
5. Test plasmid selection and maintenance in these strains using plasmids possessing a ColEI/pMB1 ori and no lacO sequences (to avoid ORT selection).

The cloning steps required for the construction of this oriSELECT strain are described in more detail below:

Splicing PCR to Produce the RNAII-lacI Fusion

Figure 5:
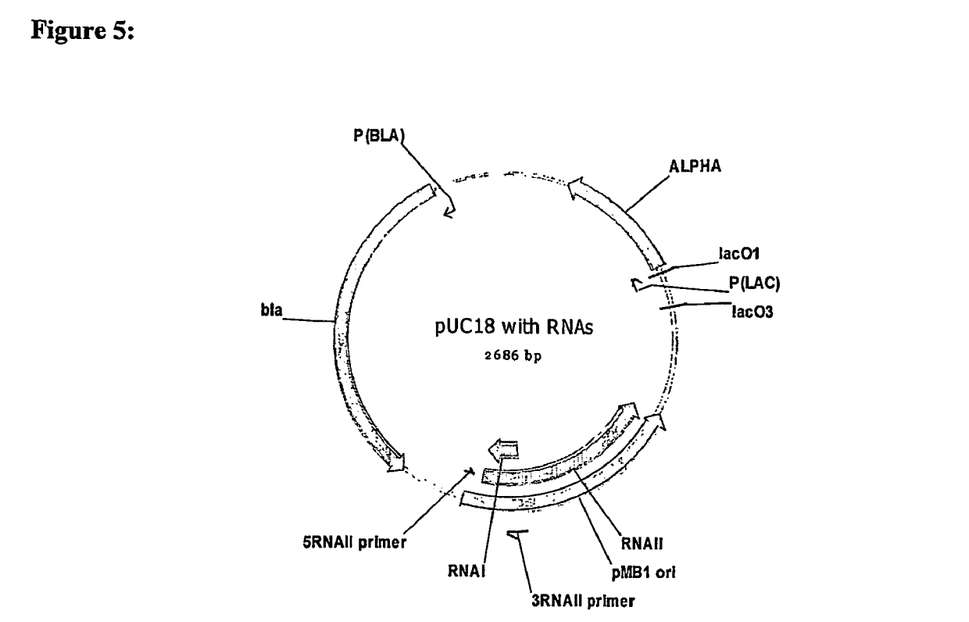
Figure 6:
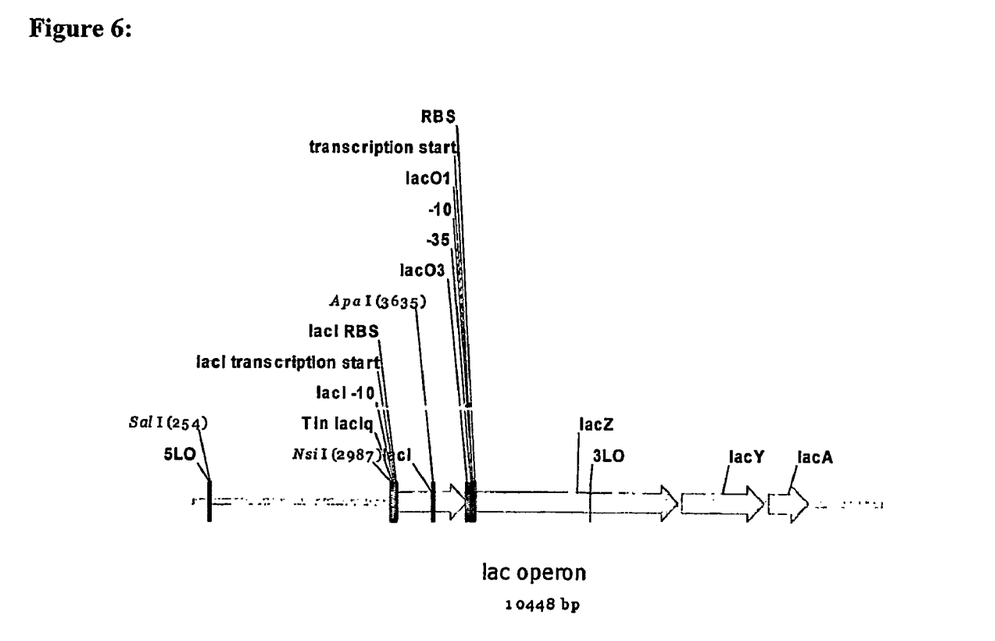
FIG. 6: Amplification of the 5'end of lacI from genomic DNA of DH1 ORT strain using PCR. The positions of the primers 5lacI and 3lacI used in the amplification are shown.
Figure 7:
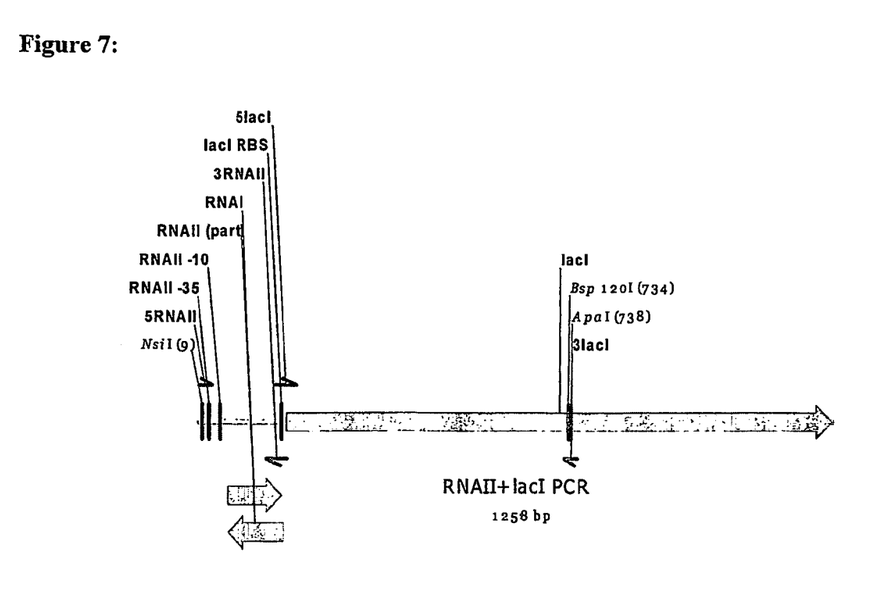
FIG. 7: Product formed by combining the RNAII amplification product produced using the primers in FIG. 5 and the lacI amplification produced using the primers in FIG. 6. Positions of primer used in the amplification of the combination produce are shown.

1. Amplify part of the 5' end of RNAII from pUC18 by PCR using the following primers (product=176 bp), as shown in FIG. 5. 5RNAII: GAATGCATCAAAGGATCTTCT-TGAGA (26 nt) (SEQ ID NO:1) 3RNAII: ACATTCAC-CACCGTATTTGGTATCTGCGCTCTGCT-GAAGCCA (42 nt) (SEQ ID NO:2).
2. Amplify part of the 5' end of lacI from DH1 gDNA by PCR using the following primers (product=597 bp), as shown in FIG. 6 5lacI: GATACCAAATACGGTGGT-GAATGTGAAACCAGTAACGTTATA (42 nt) (SEQ ID NO:3) 3lacI: ACAGAACTTAATGGGC-CCGCTAACA (25 nt) (SEQ ID NO:4).
3. Combine the two PCR products in a single PCR and amplify using 5RNAII and 3lacI primers to generate the 749 bp RNAII-lacI gene fusion PCR product (the region between 5RNAII and 3lacI primers below), as shown in FIG. 7.
4. Cut the spliced PCR product with NsiI and ApaI to generate the fragment for cloning into the lactose operon in place of the lacI promoter and 5' end.

Cloning Part of the Lactose Operon and Inserting RNAII-lacI

1. Amplify the lac operon from DH1 gDNA with the following primers. 5LO: CTCTTGCGCCGG<u>GTCGAC</u>ATACCCC (25 nt) (SEQ ID NO:5) 3LO: TAA<u>GTCGAC</u>CACGGGTTGCCGTTTT (25 nt) (SEQ ID NO:6) Primer 5LO incorporates a natural SalI site (underlined), whilst 3LO introduces one with a single nucleotide change (bold). Total PCR product size=5803 bp.
2. Cut the PCR product with SalI and clone into pUC18 cut with the same.
3. Cut this plasmid with NsiI and ApaI and clone in the fragment from step 4, replacing the promoter and 5' end of lac with the RNAII-lacI gene fusion.
4. Cut insert with SalI and ligate into pKO3recA cut with same.
5. Integrate into the chromosome of DH1lacdapD, DH1lacP2dapD and DH1lackan to produce oriSELECT strains.
6. Test plasmid selection and maintenance using plasmids with pMB1 origins of replication.

Where the RNAII constitutive promoter is used to drive RNAII-gene fusion expression, any other constitutive promoter may be substituted if required. The RNAII promoter is used in these examples as it is present already. An alternative preferred constitutive promoter is a promoter based on the optimum *E. coli* −10 and −35 sequences and spacing found in the trc promoter. This *E. coli* promoter is stranger than the RNAII promoter and may therefore be used when it is desired to product increased amounts of the LacI repressor protein, thus ensuring that growth is prevented in the absence of a plasmid. Expression of the LacI repressor protein may also be increased by increasing the distance between the 3' end of the RNAII coding region and the lacII ribosome binding site.

It will also be appreciated that alternative methods of inserting the gene cassette may be used in place of the pKO3 method described above. For example, a lambda Red recombination system may be used to integrate the cassette as a linear PCR product (Murphy, 1998, *J. Bacteriol.*, 180: 2063-2071).

The examples are based on an RNAII-gene fusion expression cassette with RNAI functioning as the antisense inhibitor. This is because in a cell containing a plasmid, RNAI is present at a 5-fold excess over RNAII (Liang et al, 1999, *J. Mol. Biol.* 292: 19-37), and so RNAI may serve as a more effective inhibitor as there should be a molar excess of RNAI available. However, there may be situations where it would be advantageous to construct the gene fusions using RNAI rather than RNAII. In this case, it will be the RNAII transcript from the plasmid that will act as the antisense inhibitor.

The chromosomal integration of the gene expressing the Rom protein from the ColEI/pMB1 ori may be necessary in oriSELECT strains, as this will increase the binding affinity of RNAI with RNAII (Chan et al, 1984 *J. Biol. Chem.* 260: 8925-8935).

---

The invention claimed is:

1. An isolated transformed host cell comprising
   i) a chromosomal gene which inhibits cell growth operably linked to a regulatory sequence; and
   ii) a plasmid comprising an origin of replication encoding an antisense sequence which binds to mRNA transcribed from the regulatory sequence,
   wherein the binding of the antisense sequence encoded by the origin of replication of the plasmid to mRNA transcribed from the regulatory sequence inhibits the action of the chromosomal gene, thereby permitting cell growth.

2. An isolated transformed host cell according to claim 1 wherein the plasmid comprises a cloning site for insertion of a gene of interest.

3. An isolated transformed host cell according to claim 2, wherein the plasmid further comprises a gene of interest.

4. An isolated transformed host cell according to claim 1, wherein the antisense sequence encoded by the plasmid is RNAI or a portion thereof and the regulatory sequence operatively linked to the chromosomal gene encodes RNAII or a portion thereof.

5. An isolated transformed host cell according to claim 1, wherein the antisense sequence encoded by the plasmid is RNAII or a portion thereof and the regulatory sequence operatively linked to the chromosomal gene encodes RNAI or a portion thereof.

6. An isolated transformed host cell according to claim 1, wherein the cell is in culture in vitro.

7. An isolated transformed host cell according to claim 1 which is a prokaryotic cell.

8. An isolated transformed host cell according to claim 7 which is a bacterial cell.

9. An isolated transformed host cell according to claim 8, wherein the cell is a gram negative bacterial cell.

10. An isolated transformed host cell according to claim 9, wherein the cell is an *E. coli* cell or a *Salmonella* cell.

11. An isolated transformed host cell according to claim 8, wherein the cell is a gram positive bacterial cell.

12. An isolated transformed host cell according to claim 11, wherein the cell is a *Bacillus* cell.

13. An isolated transformed host cell according to claim 8 which is an attenuated cell.

14. An isolated transformed host cell according to claim 1 wherein the cell is a eukaryotic cell.

15. An isolated transformed host cell according to claim 14 wherein the cell is a fungi.

16. An isolated transformed host cell according to claim 14, wherein the cell is a plant cell.

17. An isolated transformed host cell according to claim 14 wherein the cell is an animal cell.

18. An isolated transformed host cell according to claim 1, wherein the chromosomal gene is a toxin gene.

19. An isolated transformed host cell according to claim 18, wherein the toxin gene is sacB.

20. An isolated transformed host cell according to claim 1, wherein the chromosomal gene encodes a repressor protein that inhibits expression of a second chromosomal gene essential for cell growth.

21. An isolated transformed host cell according to claim 20, wherein the second chromosomal gene is conditionally essential for cell growth.

22. An isolated transformed host cell according to claim 20 wherein the chromosomal gene encodes the repressor lacI and the second chromosomal gene is operatively linked to a lac operator and promoter.

23. An isolated transformed host cell according to claim 20 wherein the chromosomal gene is dapD or fabA.

24. An isolated transformed host cell according to claim 1, wherein the chromosomal gene encodes an antisense sequence that inhibits expression of a second chromosomal gene essential for cell growth.

25. An isolated transformed host cell according to claim 24, wherein the antisense sequence encoded by the chromosomal gene inhibits expression of the second chromosomal gene by binding to the chromosomal gene.

26. An isolated transformed host cell according to claim 24, wherein the antisense sequence encoded by the chromosomal gene inhibits expression of the second chromosomal gene by binding to mRNA transcribed from the second chromosomal gene.

27. An isolated transformed host cell according to claim 24 wherein the second chromosomal gene is conditionally essential for cell growth.

28. An isolated transformed host cell according to claim 24, wherein the second chromosomal gene is dapD or fabA.

29. An isolated transformed host cell according to claim 1 wherein the chromosomal gene operably linked to a regulatory sequence is under the control of a constitutive promoter.

30. An isolated transformed host cell according claim 1 wherein the chromosomal gene operably linked to a regulatory sequence is under the control of an inducible promoter.

31. A method of maintaining a plasmid in a host cell in vitro comprising the step of culturing an isolated transformed host cell according to claim 1 under conditions sufficient to permit said cell to grow.

32. A method of producing plasmid DNA comprising culturing an isolated transformed host cell according to the method of claim 31 and isolating the plasmid DNA.

33. A method of producing a recombinant protein comprising culturing an isolated transformed host cell comprising a plasmid encoding a protein of interest according to the method of claim 31 and isolating the protein from the cell.

34. A composition comprising an isolated transformed host cell according to claim 1 together with a pharmaceutically acceptable excipient, diluent or buffer.

35. A method of delivering a gene to a patient comprising administering to the patient an isolated transformed host cell according to claim 3, wherein the isolated transformed host cell is suitable for veterinary or human therapeutic use.

36. A method of maintaining a plasmid in a recipient organism comprising introducing an isolated transformed host cell according to claim 1 into said organism, wherein said chromosomal gene in said transformed host cell is essential for cell growth in vivo and the transformed host cell is suitable for veterinary or human therapeutic use.

37. A method of immunizing a patient against a disease caused by a pathogen comprising administering an isolated transformed host cell according to claim 1 to the patient, wherein the isolated transformed host cell is suitable for veterinary or human therapeutic use.

* * * * *

SEQUENCE LISTING

```
<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
```

-continued

```
<223> OTHER INFORMATION: Oligonucleotide primer

<400> SEQUENCE: 1
gaatgcatca aaggatcttc ttgaga                                              26

<210> SEQ ID NO 2
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 2
acattcacca ccgtatttgg tatctgcgct ctgctgaagc ca                            42

<210> SEQ ID NO 3
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 3
gataccaaat acggtggtga atgtgaaacc agtaacgtta ta                            42

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 4
acagaactta atgggcccgc taaca                                               25

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 5
ctcttgcgcc gggtcgacat acccc                                               25

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 6
taagtcgacc acgggttgcc gtttt                                               25
```